United States Patent [19]

Grandadam

[11] Patent Number: 5,173,483
[45] Date of Patent: Dec. 22, 1992

[54] OVULATION STIMULATING METHOD

[75] Inventor: J. A. Grandadam, Saint Maur des Fosses, France

[73] Assignee: Roussel Uclaf, Paris, France

[21] Appl. No.: 578,894

[22] Filed: Sep. 5, 1990

[30] Foreign Application Priority Data

Sep. 7, 1989 [FR] France .................................. 89 11699

[51] Int. Cl.⁵ ..................... A61K 31/56; A61K 31/58; A61K 31/585
[52] U.S. Cl. ..................................... 514/178; 514/169; 514/170; 514/172; 514/175; 514/177; 514/179; 514/180; 514/181; 514/182
[58] Field of Search ............... 514/169, 170, 174, 175, 514/177, 178, 179, 180, 181, 182

[56] References Cited

U.S. PATENT DOCUMENTS 4,386,085  5/1983  Teutsch et al. ...................... 514/179
4,547,493 10/1985  Teutsch et al. ...................... 514/179

Primary Examiner—Frederick E. Waddell
Assistant Examiner—Kimberly Jordan
Attorney, Agent, or Firm—Bierman and Muserlian

[57] ABSTRACT

A method of stimulating ovulation in warm-blooded animals comprising administering to warm-blooded animals an ovulation stimulating effective amount of at least one anti-progestomimetic compound.

15 Claims, 1 Drawing Sheet

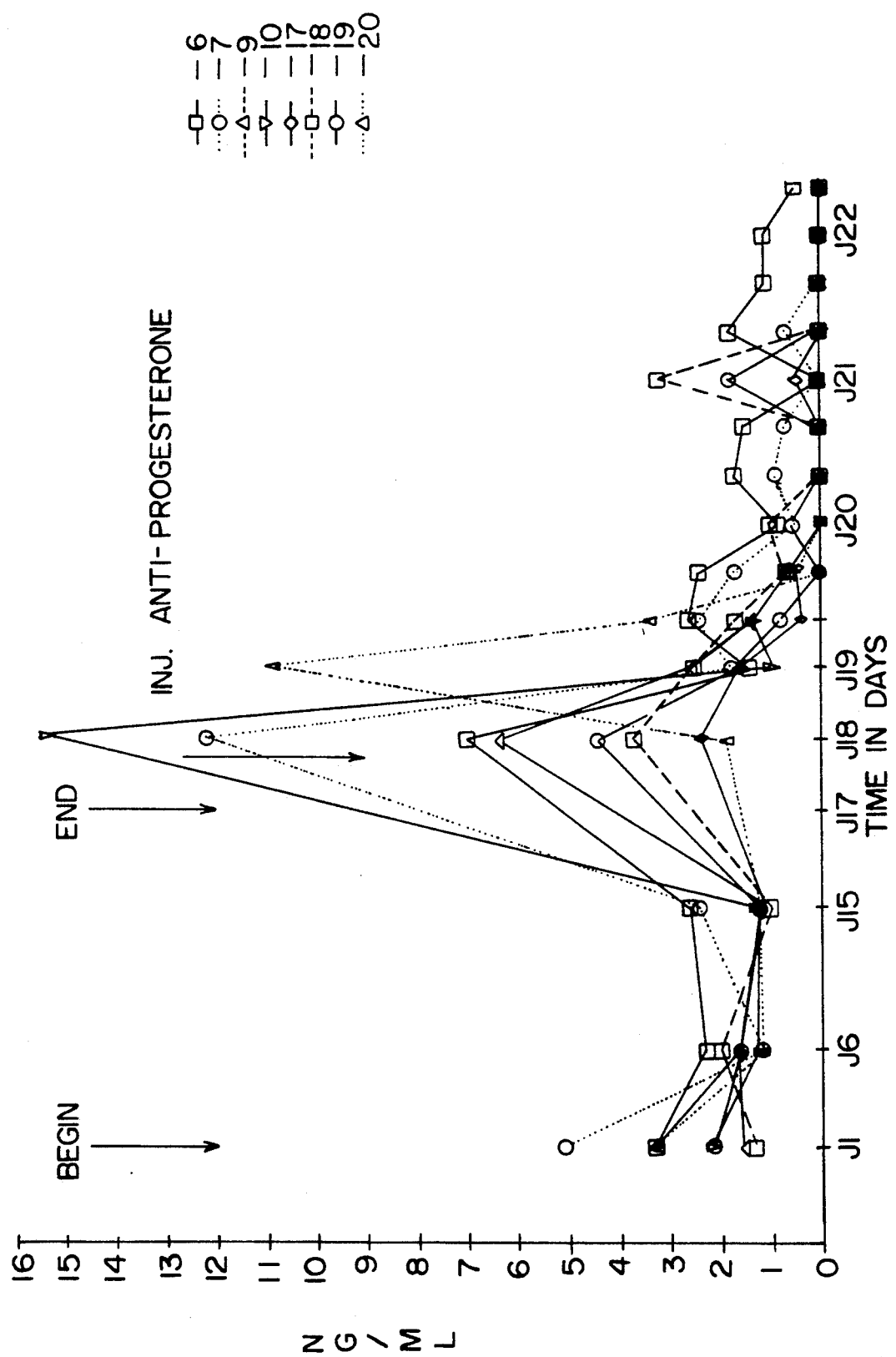

OVULATION STIMULATING METHOD

STATE OF THE ART

Pertinant to the invention is U.S. Pat. No. 4,386,085 and the prior art cited during the prosecution thereof.

OBJECTS OF THE INVENTION

It is an object of the invention to provide a novel method of stimulating ovulation in warm-blooded animals.

This and other objects and advantages of the invention will become obvious from the following detailed description.

THE INVENTION

The novel method of the invention for stimulating ovulation in warm-blooded animals, including humans, comprises administering to warm-blooded animals an ovulation stimulating effective amount of at least one anti-progestomimetic compound.

Preferably, the anti-progestomimetic compound has the formula

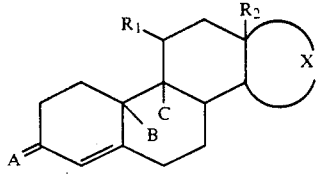

wherein $R_1$ is a hydrocarbon of 1 to 18 carbon atoms optionally interrupted by at least one heteroatom and linked to the steroid nucleus by a carbon atom, $R_2$ is a hydrocarbon of 1 to 8 atoms, X is the remainder of a 5 or 6 carbon ring optionally unsaturated and optionally substituted, A is selected from the group consisting of free or ketal radical oxo,

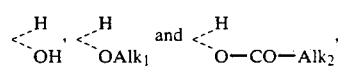

=NOH, =NOAlk$_3$ and =CH$_2$, Alk$_1$, Alk$_2$ and Alk$_3$ are individually alkyl of 1 to 8 carbon atoms or aralkyl of 7 to 15 carbon atoms, B and C form a double bond or are —O— and their non-toxic, pharmaceutically acceptable salts with acids and bases.

Among the preferred compounds of formula I are those wherein $R_1$ is a hydrocarbon of 1 to 18 carbon atoms optionally interrupted by at least one member of the group consisting of nitrogen, sulfur, phosphorus and silicium or substituted by acyl, those wherein $R_2$ is alkyl of 1 to 4 carbon atoms such as methyl, ethyl, n-propyl and butyl, those wherein Alk$_1$, Alk$_2$ and Alk$_3$ are alkyl such as methyl, ethyl, n-propyl and isopropyl or aralkyl such as benzyl and the acyl is preferably acetyl or propionyl.

Examples of suitable acids to form the acid addition salts are inorganic acids such as hydrochloric acid, hydrobromic acid, nitric acid, sulfuric acid and phosphoric acid and organic acids such as acetic acid, formic acid, propionic acid, maleic acid, fumaric acid, succinic acid, tartaric acid, citric acid, oxalic acid, glyoxylic acid, aspartic acid, alkansulfonic acids such as benzene- or p-toluene sulfonic acid and arylcarboxylic acids such as benzoic acid.

Examples of suitable bases to prepare the bases are alkali metal, alkaline earth metal and ammonium salts wherein the metals are sodium, potassium, calcium and magnesium or amines such as lysine, arginine, cysteine, betaine, carnitine, meglumine, quinine, sarcosine, procaine, histidine and N-methyl glucamine.

X preferably is the remainder of an optionally substituted pentagonal ring.

The compounds of formula I are known compounds described in European Pat. No. 0,057,115 and No. 0,262,188 and U.S. Pat. Nos. 2,566,779 and 2,625,505, as well as French applications Ser. No.89 10648 and No. 89 11173 where they are presented as being endowed with various pharmacological properties and especially with an anti-progestomimetic activity.

Other preferred compounds of formula I are those wherein B and C form a double bond, those wherein $R_2$ is methyl, those wherein A is =O, those wherein $R_1$ is selected from the group consisting of substituted aryl or aralkyl and notably:

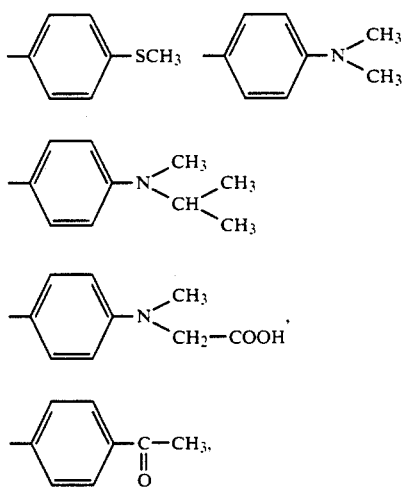

and where appropriate, in salified form, those wherein X is the remainder of

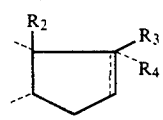

wherein $R_2$ has the above definitions and $R_3$ and $R_4$ are individually selected from the group consisting of hydrogen, —OH, —OAlk$_4$, —OCOAlk$_5$, alkenyl and alkynyl of 2 to 8 carbon atoms optionally substituted with halogen, —CO—CH$_2$—OH, —CO—CH$_2$—O—CO—Alk$_4$, —CO—COOH, —CO—COOAlk$_7$, —CHO, —CN and —CO—NHAlk$_8$, Alk$_4$, Alk$_5$ and Alk$_8$ are alkyl of 1 to 8 carbon atoms or aralkyl of 7 to 15 carbon atoms, Alk$_7$ is alkyl of 1 to 8 carbon atoms, or $R_3$ is selected from the group consisting of —OH, —OAlk$_4$ and OCOAlk$_5$ and $R_4$ is —B—O—CO—A'—Z, A' is selected from the group consisting of a bivalent aromatic and optionally unsaturated bivalent aliphatic of 1 to 6 carbon atoms optionally interrupted or terminated with a bivalent aromatic, B is an optionally unsaturated bivalent aliphatic of 1 to 8 carbon atoms, Z is —COOH optionally salified with an alkali metal, alkaline earth metal, —NH$_4$ or an amine or $R_3$ is —COA′Z and R4 is selected from the group consisting of —C≡C—R5, —CH=CH—R5 and —CH2—CH2—R5, R5 is selected from the group consisting of hydrogen, halogen, trialkylsilyl of 3 to 12 carbon atoms, alkyl of 1 to 6 carbon atoms and phenyl, the latter two being optionally substituted or R3 and R4 together with the carbon atom to which they are attached form a member of the group consisting of

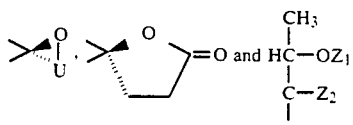

U is —(CH2)$_{n2}$— or —CH=CH—(CH2)$_{n3}$—, n2 is 1, 2, 3 or 4, n3 is 1 or 2, Z2 is alkyl of 1 to 8 carbon atoms and Z1 is selected from the group consisting of hydrogen, alkyl of 1 to 8 carbon atoms and acyl of an organic carboxylic acid of 1 to 8 carbon atoms, and notably those wherein X is the remainder of

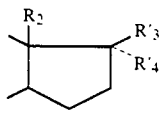

wherein R′3 is selected from the group consisting of —OH and optionally salified —CO—(CH2)2—COOH and R′4 is selected from the group consisting of alkenyl and alkynyl of 2 to 4 carbon atoms, —CH=CH—CH2—O—CO—(CH2)2—COOH and —C≡C—CH2—O—CO—(CH2)2—COOH, both optionally salified.

Among specific preferred compounds of formula I are 11β-[(4-dimethylamino)-phenyl]-17α-(1-propynyl)-estra-4,9-dien-17β-ol-3-one [product A],
sodium and [(Z)-3-[11β-[4-(dimethylamino)-phenyl]]-estra-4,9-dien-17β-ol-3-one-17α-yl]-2-propenyl]succinate,
sodium and [3-[11β-[4-(dimethylamino)-phenyl]-estra-4,9-dien-17β-ol-3-one-17α-yl]-2-propynyl]succinate,
[11β-[4-(dimethylamino)-phenyl]-17α-(1-propynyl)-estra-4,9-dien-3-one-17β-yl]acid succinate,
sodium and [11β-[4-(dimethylamino)-phenyl]-17α-(1-propynyl)-estra-4,9-dien-3-one-17β-yl]succinate,
sodium and [11β-[4-(dimethylamino)-phenyl]-17α-[(Z)-1-propenyl]-estra-4,9-dien-3-one-17β-yl]succinate,
sodium and [21-chloro-11β-[4-(dimethylamino)-phenyl]-19-nor-17α-pregna-4,9-dien-3-one-20-yn-17β-yl]succinate,
sodium and [11β-[4-(methylthio)-phenyl]-17α-(1-propynyl)-estra-4,9-dien-3-one-17β-yl]succinate,
sodium and [11β-(4-acetyl-phenyl)-17α-(1-propynyl)-estra-4,9-dien-3-one-17β-yl]succinate;
sodium and [11β-[4-(N-methyl isopropylamino)-phenyl]-17α-(1-propynyl)-estra-4,9-dien-3-one-17β-yl]succinate,
sodium salt of [[[4-[17α-(1-propynyl)-estra-4,9-dien-17β-ol-3-one-11β-yl]-phenyl]-methylamino]-acetic acid,
sodium salt of [[[4-[17α-(2-propenyl)-estra-4,9-dien-17β-ol-3-one-11β-yl]-phenyl]-methylamino]-acetic acid,
sodium salt of [[4-(21-chloro-19-nor-17α-pregna-4,9-dien-17β-ol-3-one-20-yn-11β-yl)-phenyl]-methylamino]-acetic acid, (17R)-11β-[4-(methylthio)-phenyl]-spiro-(estra-4,9-dien-17,-2′(5H)-furan)-3-one,
(17R)-11β-(4-acetyl-phenyl)-spiro-(estra-4,9-dien-17,2′-(5H)-furan)-3-one,
11β-[4-(dimethylamino)-phenyl]-17α-(2-propenyl)-estra-4,9-dien- 17β-ol-3-one,
11β-[4-[methyl-(3-methylbutyl)amino]-phenyl]-17α-(1-propynyl)-estra-4,9-dien-17β-ol-3-one,
11β-[4-(dimethylamino)-phenyl]-17α-[(Z)-1-propenyl]-estra-4,9-dien-17 -ol-3-one and 11 -[4-(dimethylamino)-phenyl]-17-propyl-estra-4,9-dien-17β-ol-3-one and
11β-[4-(dimethylamino)-phenyl]-17α[(Z)-1-propenyl]-estra-4,9-dien-17β-ol-3-one (product B).

The compounds can be prepared as in European Pat. Nos. 0,057,115 and 0,262,188 as well as in U.S. Pat. Nos. 2,566,779 and 2,625,505. The compounds not described in these patents can be prepared by one of the processes hereafter.

The process for the preparation of compounds of the formula

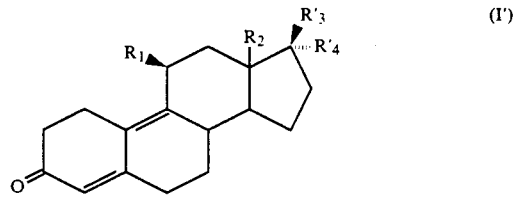

wherein R2 is aliphatic hydrocarbon of 1 to 18 carbon atoms, R1 is a hydrocarbon of 1 to 18 carbon atoms optionally containing at least one heteroatom and linked to the steroid nucleus by a carbon atom, R′3 is —OH, OAlk4 or OAlk5, Alk4 and Alk5 having the above definitions and R′4 is —B—O—CO—A′—Z wherein A′, B and Z have the above definitions or R′3 is —CO—A′—Z wherein A′and Z have the above definitions and R′4 is —C≡C—R5, —CH=CH—R5— or —CH2—CH2—R5 and R5 has the above definitions comprises reacting a compound of the formula

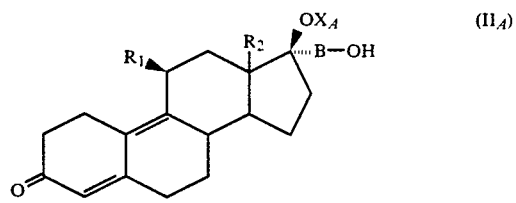

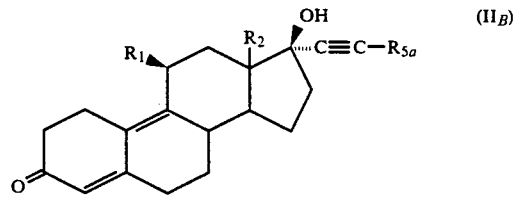

wherein R1 and R2 have the above definitions and R5a has the definition of R5 with the reactive groups protected in a neutral solvent and in the presence of a base with a compound of the formula

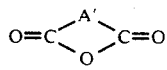

to obtain if necessary after deprotection of the reactive groups and optional salification of the carboxy compounds of the formula

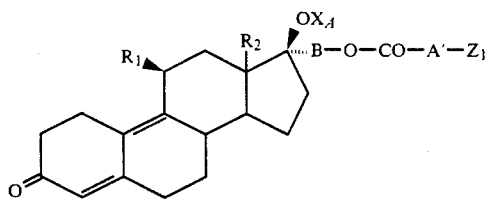

wherein $Z_1$ is an optionally salified carboxy or with a compound of the formula HOOC—A'—U or a functional derivative thereof wherein U is —COOH or —COOR$_3$, Re is alkyl 1 to 6 carbon atoms or aralkyl of 7 to 12 carbon atoms to obtain after deprotection of any protected group a compound of the formula

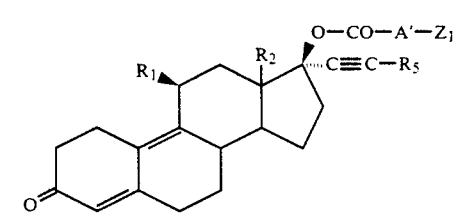

when U is free carboxy optionally salified are compounds of formula $I_{A1}$ and $I_{B1}$ and when U is —COOR$_e$ correspond to compounds of the formula which are then hydrolyzed or saponified to obtain the compounds of formula $I_{A1}$ and $I_{B1}$.

The compounds of formula $I_{B1}$ and $IV_D$ may be reacted with a hydrogenation agent of triple bonds to obtain a compound of the formula and optionally subjecting the latter to a hydrogenation agent for double bonds to obtain the compounds of the formula or to an agent for direct hydrogenation of the triple bonds into single bonds to obtain the products of formulae $I_{B3}$ and $VI_D$ respectively, and the compounds of formula $V_D$ and $VI_D$ may be hydrolyzed or saponified to obtain the compounds of formulae $I_{B2}$ and $I_{B3}$, respectively.

In a preferred mode of the process, the reaction of the compound of formula III, with the compounds of formulae $II_A$ and $II_B$ is effected in the presence of a base and a neutral solvent with any hydroxy in $R_5$ protected a (2-tetrahydropyranyloxy) by earlier reaction with 2,3-dihydropyran. The removal of the said protective group is effected with an acid or with an acidic sulfonic resin. Examples of the neutral solvent are ether, acetonitrile, chloroform and methylene chloride and examples of the base are triethylamine, diisopropylamine, 4-dimethylamino-pyridine, pyridine and N-methyl-morpholine.

The triple bond hydrogenation agent to form the double bond may be hydrogen in the presence of a catalyst such as palladium on barium sulfate and the hydrogenation agent for the conversion a double or triple bond into a single bond may be hydrogen in the presence of a catalyst such as palladium on activated charcoal or chloro tris(triphenylphosphine) rhodium.

Examples of functional derivatives of the acids of formula $III_2$ are the anhydrides formed in situ by reaction with alkyl chloroformates such as isobutyl chloroformate or with a dicycloalkylcarbodiimide such as dicyclohexylcarbodiimide. The hydrolysis and saponification of —COOR$_e$ as well as salification of any carboxy functions may be effected in known ways.

The starting materials of formula $II_A$ and $II_B$ for the formation of the compounds of formula I' are generally known and described in French Pat. Nos. 2,377,418, 2,497,807, 2,522,328 and 2,528,434 and European Pat. Nos. 057,115 and 190,759. Some of the compounds of formula $III_1$ and $III_2$ are commerically avaiable and the others may be prepared by known procedures such as those described in ETAIX, annales de Chimie (7) Vol. 9 p. 371, LOVEN, J. Prakt. Chimie (2) Vol. 29, p. 376 and UHLENBROEK, Recueil des Travaux Chimiques des Pays-Bas (1957) Vol. 76. p. 129 to 142.

The compounds of the formula

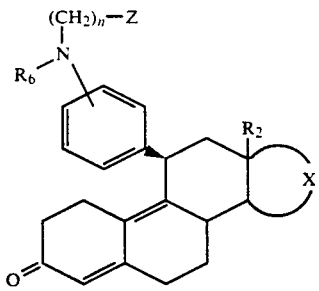

(I″)

wherein $R_2$ is an aliphatic hydrocarbon of 1 to 8 carbon atoms, $R_6$ is hydrogen or alkyl of 1 to 12 carbon atoms and optionally substituted, n is an integer from 1 to 6, Z is carboxy free or salified in the form of an alkali metal or alkaline earth metal salt, an ammonium salt or an amine salt, X is the remainder of a pentagonal or hexagonal ring optionally substituted and optionally unsaturated by reacting the products of the formulae

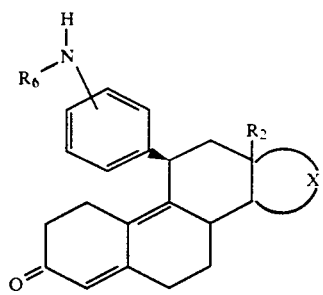

VII$_A$

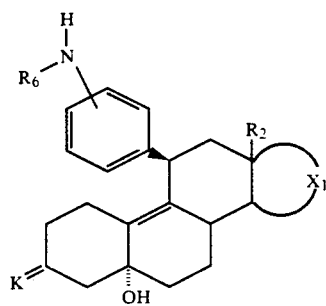

VII$_B$ wherein $R_2$, $R_6$ and X are as defined aove $X_1$ has the value for X optionally with any reactive functions protected, and K is a protected oxo in the presence of a base with halo ester of the formula $$Hal—(CH_2)_n—COOR_7 \quad VIII$$

wherein Hal is halogen, n has the above meaning and $R_7$ is alkyl of 1 to 4 carbon atoms and optionally substituted by one or more phenyls to obtain the products of the formulae

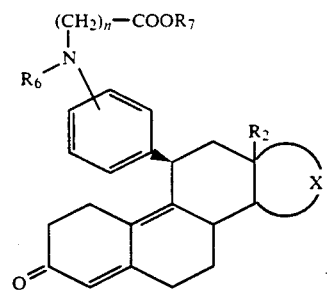

IX$_A$

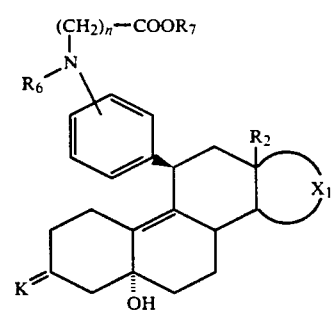

IX$_B$ respectively and the products of formula IX$_B$ are subjected to a dehydration reaction and to an optional deprotection of the protected reactive functions to obtain the products formula IX$_A$, and the latter product are subjected to a basic treatment then, if desired, an acid treatment to obtain the products of formula I".

The nitrogen base used with ethyl bromoacetate is preferably triethylamine. The hydrogenation of the triple bonds into double bonds takes place in the presence of a catalyst such as palladium hydroxide on barium sulfate and complete hydrogenation into a single bond takes place preferably in the presence of chlorotris(triphenylphosphine) rhodium.

Some of the products of formula VIII are commercially available products and the others can be prepared by known methods such as in MOUREU et al, comptes rendus de l'Academie des Sciences, Vol. 172, p. 1268 and Annales de Chimie [9] Vol. 15 p. 233. The products of formulae $VII_A$ and $VII_B$ are generally known and their preparation is described in European Pat. Nos. 0,262,188; 0,095,572 and 0,057,115 and French Pat. Nos. 2,566,779 and 2,620.707.

In a preferred embodiment of the method of the invention, the antiprogestomimetic compounds are administered after a progesterone or progestomimetic treatment with a progesterone or 17α-allyl-estra-4,9,11-triene-17β-ol-3-one (Product C) described in French Medical Pat. No. 5183 M.

One of the preferred methods is the use in veterinary medicine after an estrus synchronization treatment which itself does not appear to have a positive effect on ovulation. The present method has the advantage of increasing or stimulating ovulation is of great interest for breeding, especially commercial breeding.

In a preferred embodiment, a tampon soaked with progesterone at a dose of between 0.5 and 2.5 g per animal, for example between 1.3 g and 1.6 g per animal, is used for the estrus synchronization treatment. In another preferred embodiment, a treatment of 20 to 60 mg of product C per day and per animal for 10 to 30 days, administered orally in the food, for example, a 15 to 20 day treat-ment of 35 to 45 mg of product C, is used for the estrus synchronization treatment. Then, the anti-progestomimetic product or products are administered after a synchronization treatment, preferably with a single injection, for example a single injection of product A or B at a dose of between 0.5 to 5000 mg per animal, and preferably at a dose of between 500 and 5000 mg per animal.

Examples of breeding animals, cattle, sheep, goats, pigs, horses as well as dogs and cats. Preferably, the animals are cows and notably heifers.

The method to the invention includes a human medicine for the treatment of ovulatory disorders, ovulatory dysfunction and even an ovulation which enables the combatting of certain forms of sterility. Therefore the method may be applied to women for the treatment of certain forms of sterility.

In the following examples there are described several preferred embodiments to illustrate the invention. However, it should be understood that the invention is not intended to be limited to the specific embodiments.

EXAMPLE 1

Sodium and [(Z)-3-[11β-4-(dimethylamino)-phenyl]-estra-4,9-dien-17β-ol-3-one-17α-yl]-2-propenyl] succinate STEP A: (Z)-3-[11β-[4-dimethylamino)-phenyl]-estra-4,9-dien-17β-ol-3 one-17α-yl]-2-propenyl acid succinate 900 mg of 11β-[4-(dimethylamino)-phenyl]-17α-[(Z)-3-hydroxy-1-propenyl]-estra-4,9-dien-17α-ol-3-one were dissolved in 9 ml of chloroform in a flask provided with a magnetic stirrer and then 304 mg of succinic anhydride and 1.45 ml of triethylamine were added. The mixture was stirred for 15 hours at ambient temperature, then evaporated to dryness. The 1.443 g of residue were purified by chromatography on a silica column (eluant: (ethyl acetate 90 —cyclohexane 10)—3% acetic acid). After crystallization from a methanol—water mixture (60-40), 695 mg of the desired product in the form of yellow crystals melting at approx. 145° C. were obtained.

Thin layer chromatography was Rf=0.60. (support: KC 18 Whatman ®; eluant: methanol—0.05 molar aqueous solution of ammonium acetate (80-20)).

STEP B: Sodium and [(Z)-3-[11β-[4-(dimethylamino)-phenyl]-estra-4,9-dien-17β-ol-3-one-17α-yl]-2-propenyl] succinate 93 mg of sodium bicarbonate were dissolved in 20 ml of water in a flask provided with a magnetic stirrer and then a solution of 639 mg of the product of Step A in 20 ml of ethanol was added dropwise. The ethanol was expelled by azeotropy and the aqueous solution was filtered on a millipore ® membrane (0.45 micron), then lyophilized to obtain 654 mg of the desired product in the form of a cream-colored powder with a specific rotation of $[\alpha]_D = 101° + 2°$ (c=1% in water). Thin layer chromatography: Rf=0.62. (support: KC 18 Whatman ®; eluant: methanol—0.05 molar aqueous solution of ammonium acetate (80-20)).

EXAMPLE 2

Sodium and [3-[11β-[4-(dimethylamino)-phenyl]-estra-4,9-dien-17β-ol-3-one-17α-yl]-2-propynyl] succinate STEP A: [3-[11β-[4-(dimethylamino)-phenyl]-estra-4,9-dien-17β-ol-3-one-17α-yl]-2-propynyl] acid succinate 900 mg of 11β-[4-dimethylamino)-phenyl]-17α-(3-hydroxy-1-propynyl)-estra-4,9-dien-17β-ol-3-one were dissolved in 9 ml of chloroform in a flask provided with a magnetic stirrer and then 303 mg of succinic anhydride and 1.4 ml of triethylamine were added. The mixture was stirred for 17 hours at ambient temperature. After evaporated to dryness, the 1.685 g of crude product was purified by chromatography on a Bondapack C 18 ® column (eluting with a mixture of methanol and a 0.05 molar aqueous solution of ammonium acetate (60-40)) to obtain 1.104 g of the desired product with a Rf=0.63 (thin layer chromatography, support: KC 18 Whatman ® eluant: methanol—0.05 molar aqueous solution of ammonium acetate (80-20)).

STEP B: Sodium and [3-[11β-[4-dimethylamino)-phenyl]-estra-4,9dien-17β-ol-3-one-17α-yl]-2-propynyl] succinate Using the procedure of Example 1, 141 mg of sodium bicarbonate in 29 ml of water and 964 mg of the product of Step A in 29 ml of ethanol were reacted to obtain 935 mg of the desired product having a specific rotation of $[\alpha]_D = +55° + 1.5°$ (c=1% in water) and a Rf=0.63 (thin layer chromatography, support: KC 18 Whatman ® eluant: methanol—0.05 molar aqueous solution of ammonium acetate (80-20)).

EXAMPLE 3

[11β-[4(dimethylamino)-phenyl]-17α-(1-propynyl)-estra-4,9-dien-3-one-17β-yl] acid succinate The reaction mixture was prepared by adding 2.15 g of succinic anhydride, 2.2 ml of triethylamine and 215 mg of 4-(dimethylamino)-pyridine to a solution of 2.15 g of 11β-[4-(dimethyl-amino)-phenyl]-17α-(1-propynyl)-estra-4,9-dien-17β-ol-3-one in 22 ml of chloroform. The mixture was refluxed for 42 hours and 430 mg of 4-(dimethylamino)-pyridine and 4.4 ml of triethylamine were added.

Reflux was continued for 26 hours and the solution was poured into a mixture of water and ice. After decanting the organic phase, the latter was washed with water then dried, and the chloroform was distilled off to obtain a brown-colored dry extract. The aqueous phase was acidified with 0.5N hydrochloric acid, then neutralized by the addition of sodium acetate. Extraction was carried out again with ethyl acetate and the new organic phase was washed with water, dried, and after distillation of the solvent, a residue was produced which was combined with the first organic phase. The product was purified on a silica column by eluting with a mixture of ether - ethyl acetate (9-1) with 3% acetic acid and crystallized twice from an ether - methylene chloride mixture to obtain 1.435 g of the desired product with a melting point of approx. 165° C. and a specific rotation of $[\alpha]_D = +97°$ (c=0.8% in CHCl$_3$). Rf=approx. 0.40 (thin layer chromatography, support: SiO$_2$, eluant: ether (9) - ethyl acetate (1) 3% acetic acid).

EXAMPLE 4

Sodium and [11β-[4 (dimethylamino)-phenyl]-17α-(1-propynyl)-estra-4,9-dien-3-one-17β-yl] succinate 3 g of the product of Example 3 and 94 ml of ethanol were introduced into a flask provided with a magnetic stirrer and then a solution of 433 mg of sodium bicarbonate in 94 ml of water was poured in. After 30 minutes of stirring at ambient temperature, the ethanol was expelled by azeotropy and the remaining solution was filtered on a millipore ®membrane (0.45 microns) and lyophilized to obtain 2.88 g of desired product with a specific rotation of $[\alpha]_D = +48.5° \pm 1.5°$ (c=1% in water) and a Rf=0.54 (thin layer chromatography, support: KC 18 Whatman ®, eluant: methanol—0.05 molar aqueous solution of ammonium acetate (80- 20)).

EXAMPLE 5

Sodium and [11β-[4-(dimethylamino)-phenyl]-17α-[(Z)-1-propenyl-estra-4,9-dien-17β-yl] succinate STEP A:
[11β-[4-(dimethylamino)-phenyl]-17α-[(Z)-1-propenyl]-estra-4,9-dien-3-one-17β-yl] acid succinate 2.462 g of the product of Example 3 were put in a flask provided with a magnetic stirrer and 150 ml of ethyl acetate with 2% pyridine, 15 ml of water and 50 mg of 10% palladium hydroxide on barium sulfate were added. After hydrogenation with stirring for 5 hours and 30 minutes, the reaction mixture was filtered and the pyridine wa expelled. The remaining solution was evaporated to dryness and the residue thus obtained was purified by two successive chromatographies on a Bondapack C 18 column, eluting with a mixture of methanol and a 0.05 molar aqueous solution of ammonium acetate (65-35) to obtain 576 mg of the desired product with a Rf=0.50 (thin layer chromatography, support: KC 18 Whatman ®, eluant: methanol - 0.05 molar aqueous solution of ammonium acetate (80-20))

STEP B: Sodium and [11β-[4-(dimethylamino)-phenyl]-17α-(Z)-1-propynyl]-estra-4,9-dien-3-one-17β-yl] succinate Using the procedure of Example 1, a solution of 100 mg of sodium bicarbonate in 21 ml of water and 665 mg of the product of Step A in 21 ml of ethanol were reacted to obtain 583 mg of the desired product with a specific rotation of $[\alpha]_D = +56.5° +1.5°$ (c=1% in water) and a Rf=0.50 (thin layer chromatography, support: KC 18 Whatman ®, eluant: methanol—0.05 molar aqueous solution of ammonium acetate (80.20)).

EXAMPLE 6

Sodium and 21-chloro-11β-[4-(dimethylamino)-phenyl]-19-nor-17α-pregna-4,9-dien-3-one-20-yn-17β-yl] succinate STEP A:
[21-chloro-11β-[4-(dimethylamino)-phenyl]-19-nor-17α-pregna-4,9-dien-3-one-20-yn-17β-yl] acid succinate 1.854 g of 21-chloro-11β-[4-(dimethylamino)-phenyl]-17α-pregna-4,9-dien-20-yn-17β-ol-3-one were dissolved in 18.5 ml of chloroform in a flask provided with a magnetic stirrer and then 2.497 g of succinic anhydride, 7 ml of triethylamine and 0.936 g of 4-(dimethylamino)-pyridine were added. The mixture was refluxed for 42 hours and then the reaction medium was poured into 31 ml of a 2N hydrochloric acid solution. The pH was brought to 6-7 by the addition of sodium acetate. The chloroform phase was separated, then extracted again twice with chloroform. The combined extracts were washed with water, dried on sodium sulfate, then concentrated under reduced pressure to obtain 3.85 g of a brown residue which was purified by chromatography on a kieselgel column, eluting first with ethyl ether and then with a mixture of ethyl ether with 3% acetic acid to obtain 1.8 g of crude product. The latter was crystallized from a methylene chloride - ethyl ether mixture, then from a methylene chloride - ethyl ether mixture to obtain 1.21 g of the expected product melting at approx. 165° C. and having a specific rotation of $[\alpha]_D = +63° +1.5°$ (c=0.90 in CHCl$_3$) and a Rf=0.53 - thin layer chromatography. (support: KC 18 Whatman ®, eluant: methanol—0.05 molar aqueous solution of ammonium acetate (80-20)).

STEP B: Sodium and [21-chloro-11β-[4-(dimethylamino)-phenyl]-19-nor-17α-pregna-4,9-dien-3-one-20yn-17β-yl] succinate 817 mg of the product of Step A and 25 ml of ethanol were mixed together in a flask provided with a magnetic stirrer and a solution of 113 mg of sodium bicarbonate in 25 ml of water was then added dropwise. The reaction medium was stirred for 30 minutes at ambient temperature and then the ethanol was expelled by azeotropy. The remaining solution was filtered on a millipore ® membrane (0.45 microns), then lyophillized to obtain 813 mg of lyophilizate which corresponded to the desired product with a specific rotation of $[\alpha]_D = +16.5° +1°$ (c=1% in H$_2$O) and a Rf=0.54 (thin layer chromatography; support: KC 18 What-

EXAMPLE 7

Sodium and 11β-[4-(methylthio)-phenyl]-17α-(1-propynyl)-estra-4,9-dien-3-one-17β-yl] succinate

STEP A:
[11β-[4-(methylthio)-phenyl]-17α-(1-propynyl)-estra-4,9-dien-3-one-17β-yl] acid succinate In a flask provided with a magnetic stirrer and a condensor, 1.5 g of 11β-[4-(methylthio)-phenyl]-17α-(1-propynyl)-estra-4,9-dien-17β-ol-3-one and 15.3 ml of chloroform were mixed together and then 1.86 g of succinic anhydride, 6 ml of triethylamine and 794 mg of 4-(dimethylamino)-pyridine were added. The mixture was refluxed for 94 hours, then poured into N hydrochloric acid and extracte with chloroform. The chloroform phase was washed with water, dried on sodium sulfate and the solvent was eliminated under reduced pressure at 40° C. to obtain 2.26 g of crude product which was chromatographed on a kieselgel 60H silica column (-eluant: (methylene chloride 97.5 —methanol 2.5) - 1% acetic acid). After crystal-lization from a methylene chloride - isopropyl ether mixture, 826 mg of crystals of the desired product melting at 158° C. and having a Rf=0.61 (thin layer chromatography, support KC 18 Whatman ®, eluant: mixture of ethanol—0.05 molar aqueous solution of ammonium acetate (70-30)) were obtained.

STEP B: Sodium and 11β-[4-(methylthio)-phenyl]-17α-(1-propynyl)-estra-4,9-dien-3one-17β-yl] succinate Using the procedure of Example 1, 108mg of sodium bicarbonate in 21.5 ml of water and 719 mg of the product of Step A in 21.5 ml of ethanol were reacted to obtain 720 mg of a lyophilizate corresponding to the desired product with a specific rotation of $[\alpha]_D = +74.5° +1.5°$ (c=1% in water) and a Rf=0.61 (thin layer chromatography, support: KC 18 Whatman ®, eluant: ethanol—0.05 molar aqueous solution of ammonium acetate (70-0)).

EXAMPLE 8

Sodium and [11β-(4-acetyl phenyl)-17α-(1-propynyl)-estra-4,9-dien-3-one-17β-yl] succinate

STEP A: [11β-(4-acetyl phenyl)-17α-(1-propynyl)-estra-4,9-dien-3-one-17β-yl] acid succinate 1.8 g of 11β-(4-acetyl phenyl)-17α-(1-propynyl)-estra-4,9-dien-17β-ol-3-one were dissolved in 18 ml of chloroform and 2.54 g of succinic anhydride, 7 ml of triethylamine and 0.95 g of 4-(dimethylamino)-pyridine were added. The solution was refluxed for 70 hours and after cooling down to ambient temperature, the reaction medium was poured into 2N hydrochloric acid and extracted with chloroform.

The organic phase was washed with water, dried on sodium sulfate and evaporated to dryness under vacuum. The crude product was chromatographed on a Kieselgel 60 silica column, eluting first with ethyl ether, then with ethyl ether with 3% acetic acid to obtain 1.37 g of crude product which was purified by crystallization from a methylene chloride—ethyl ether mixture, then crystallization from an identical mixture to obtain 1.027 g of the desired product melting at approx. 168° C. and having a Rf=0.32 (thin layer chromatography; support: SiO$_2$F$_{254}$ Merck 60 ®, eluant: mixture of ethyl ether—ethyl acetate with 3% acetic acid (90- 10)).

STEP B: Sodium and [11β-(4-acetyl phenyl)-17α-(1-propynyl)-estra-4,9-dien-3-one-17β-yl] succinate 0.874 g of the product of Step A were dissolved in 30 ml of ethanol and the solution was added dropwise to a solution of 0.132 g of sodium bicarbonate in 30 ml of water. Then, the ethanol was expelled by azeotropy and the aqueous solution was filtered on a millipore membrane (0.45 microns), then lyophilized to obtain 0.908 g of the desired sodium salt with a specific rotation of $[\alpha]_D = +67° +1.5°$ (c=1% in water) and a Rf=0.73 (thin layer chromatography; support: KC 18 Whatman-®eluant: mixture of methanol—0.05 molar aqueous solution of ammonium acetate (80-20)).

EXAMPLE 9

Sodium and [11β-[4-(N-methyl-isopropylamino)-phenyl]-17α-(1-propynyl)-estradien-3-one-17β-yl] succinate

STEP A:
[11β-[4-(N-methyl-isopropylamino)-phenyl]-17α-(1-propynyl)-estra-4,9-dien-3-one-17 -yl acid succinate A solution of 2.159 g of 11β-[4-(N-methyl-isopropylamino)-phenyl]- 17α-(1-propynyl)-estra-4,9-dien-17β-ol-3-one, 22 ml of triethylamine, 2.52 g of succinic anhydride, 8.1 ml of triethylamine and 1.07 g of 4-dimethylamino-pyridine was refluxed for 24 hours and 0.339 g of succinic anhydride were added and reflux was continued for 74 hours. After cooling, the reaction medium was poured into 36 ml of 2N hydrochloric acid and the pH was adjusted to 6 by the addition of sodium acetate. After the organic phase was decanted, the aqueous phase was extracted with chloroform. The combined chloroform phases were washed with water, dried on sodium sulfate and evaporated to dryness under vacuum. The residue was chromatographed on a column of 300 g of kieselgel 60 ® silica, eluting first with ethyl ether and then with ethyl ether with 3% acetic acid to obtain 1.493 g of crude product which was crystallized from a methylene chloride - ethyl ether mixture to obtain 1.082 g of the desired acid succinate melting at approx. 155° C. and having a Rf=0.47 (thin layer chromatography; support: KC 18 Whatman ®, eluant: mixture of methanol—0.05 molar aqueous solution of ammonium acetate (80-20)).

STEP B: Sodium and [11β-4-(N-methyl isopropylamino)-phenyl]-17α-(1-propynyl)-estra-4,9-dien-3-one-17β-yl] succinate Using the procedure of Example 8, 0.128 g of sodium bicarbonate in 30 ml of water and 0.933 g of the product of Step A in 30 ml of ethanol were reacted to obtain 0.915 g of the desired sodium salt with a specific rotation of $[\alpha]_D = +40.5° +1.5°$ (c=1% in water) and a Rf=0.47 (thin layer chromatography, support KC 18 Whatman ®, eluant: mixture of methanol—0.05 molar aqueous solution of ammonium acetate (80-20)).

EXAMPLE 10

Sodium salt of
[[4-[17α-(1-propynyl)-estra-4,9-dien-17β-ol-3-one-1β-yl]-phenyl]methylamino]-acetic acid

STEP A: Ethyl
[[4-[-17α-(1-propynyl)-estra-4,9-dien-17β-ol-3-one-11β-yl]-phenyl]-methylamino]-acetate 1.66 g of 11β-[4-(methylamino)-phenyl]-17α-(1-propynyl)-estra-4,9-dien-17β-ol-3-one were dissolved in 3.2 ml of triethylamine in 60 ml of benzene and 3.2 ml of ethyl bromoacetate were added to the solution which was heated under reflux and under nitrogen. After cooling, the reaction medium was diluted with an aqueous solution of sodium bicarbonate and the organic phase was extracted, then washed with water, dried and distilled. The residue was chromatographed on silica with a cyclohexane - ethyl acetate mixture (1-1) to obtain 2 g of product which was crystallized from a methylene chloride - isopropyl ether mixture to obtain 1.7 g of the desired product melting at approx. 110° C. and having a specific rotation of $[α]_D = +120°$ (c = 1% in CHCl$_3$) and a Rf = 0.36 (thin layer chromatography; support SiO$_2$; eluant: cyclohexane - ethyl acetate mixture (1-1)).

STEP B : Sodium salt of
[[4-[17α-(1-propynyl)-estra-4,9-dien-17β-ol-3-one-11β-yl]-phenyl]-methylamino]-acetic acid 0.5 g of the ester of Step A were treated with 1 ml of 1N sodium hydroxide in 10 ml of absolute ethanol at ambient temperature. After 15 hours of resting at this temperature, the solution was evaporated to dryness under reduced pressure. The residue was dissolved in the minimum amount of 50% methanol in water and chromatographed on Lichrosorb KC 18 ®. Elution was done first with methanol water (30-70) and then with 50% methanol in water to obtain 0.35 g of the desired product with a specific rotation of $[α]_D = +137°$ (c = 1% in EtOH) and a Rf = 0.6 (thin layer chromatography; support silica KC 18 Whatman ®; eluant: 70% aqueous solution of methanol).

EXAMPLE 11

Sodium salt of
[[4-[17α-(2-propenyl)-estra-4,9-dien-17β-ol-3-one-11β-yl]-phenyl]-methylamino]-acetic acid

STEP A: Ethyl
[[(4-(17α-(2-propenyl)-estra-4,9-dien-17β-ol-3-one-11β-yl]-phenyl]-methylamino]-acetate Using the procedure of Step A of Example 12, 1.068 g of 11β-[4-(methylamino)-phenyl]-17α-(2-propenyl)-estra-4,9-dien-17β-ol-3-one in 37 ml of toluene and 2.1 ml of triethylamine and 2.1 ml of ethylbromoacetate were reacted to obtain after crystallization from a methylene chloride and isopropyl ether mixture, 1.151 g of the desired product in the form of white crystals melting at 191° C and having a Rf = 0.27 (thin layer chromatography; support: silica F$_{254}$ Merck 60 ®; eluant mixture of ethyl acetate - essence G (50-50)).

STEP B: Sodium salt of
[[4-[17α-(2-propenyl)-estra-4,9-dien-17β-ol-3-one-11β-yl]-phenyl]-methylamino]-acetic acid 1.079 g of the product of Step A were dissolved in 22 ml of ethanol and 2.17 ml of N sodium hydroxide and after 3 hours of stirring at ambient temperature, 3 ml of ethanol were added. The mixture was stirred for 23 hours and the solution was filtered. The filtrate was evaporated under reduced pressure and the residue was chromatographed on KC 18 Bondapack, eluting with mixtures of methanol-water (30-70) and methanol - water (50-50). The eluate was concentrated to eliminate the methanol, filtered and lyophilized to obtain 0.878 g of the desired salt with a specific rotation of $[α]_D = +203° + 3°$ (c = 1% in EtOH) and having a Rf = 0.63 (thin layer chromatography; support KC 18 Whatman ®; eluant: methanol -water mixture (7-3)).

EXAMPLE 12

Sodium salt of
[[4-[21-chloro-19-nor-17α-pregna-4,9-dien-17β-ol-3-one-20-yn-11β-yl]-phenyl]-methylamino]-acetic acid

STEP A:
[[4-[21-chloro-19-nor-17α-pregna-4,9-dien-17β-ol-3-one-20-yn-11β-yl)-phenyl]-methylamino]-acetic acid 1.38 g of 21-chloro-11β-[4-(methylamino)-phenyl]-19-nor-17α-pregna-4,9-dien-17β-ol-20-yn-3-one were dissolved in 47 ml of toluene and 2.5 ml of triethylamine and after the addition of 2.5 ml of ethyl bromoacetate, the solution was stirred for 2 hours at 80° C. After cooling, the mixture was added to a saturated aqueous solution of sodium bicarbonate and the aqueous phase was decanted. The organic phase was washed with water, dried on sodium sulfate and evaporated to dryness under reduced pressure. The crude product was chromatographed on silica, eluting with an ethyl acetate - essence G mixture (40-60). After recrystallization from a methylene chloride - isopropyl ether mixture, 1.555 g of the desired ester melting at 105° C. and having a Rf = 0.27 (thin layer chromatogrphy; support: silica F$_{254}$ Merck 60 ®; eluant: ethyl acetate - essence G mixture (1-1)) were obtained.

STEP B: Sodium salt of [[4-(21 chloro-19-nor-17α-pregna-4,9-dien-17β-ol-3-one-20-yn-11β-yl]-phenyl]-methylamino]-acetic acid 1.494 g of the product of Step A were dissolved in 29 ml of absolute ethanol and 2.9 ml of N sodium hydroxide and the solution was stirred for 22 hours and 30 minutes at ambient temperature and filtered. The filtrate was evaporated to dryness and the residue was chromatographed on KC 18 Bondapack, eluting with mixtures of methanol - water (30-70) and then methanol - water (50-50). The eluate was concentrated to eliminate the methanol, filtered and lyophilized to obtain 1.23 g of the desired salt with a specific rotation of $[α]_D = 124° + 2.5°$ (c = 1% in EtOH) and a Rf = 0.67 (thin layer chromatography; support: KC 18 Whatman ®, eluant: methanol - water mixture (70-30).

Biological Study 30 heifers for beef consumption were used, namely 15 Charolais and 15 White - Blue Belgians and the cows which were inmature were detected by the determination of plasmatic progesterone carried out twice at 10 days intervals. The test was done on the 8 mature heifers and the animals received a treatment with 17α-allyl-estra-4,9,11-triene-17β-ol-3-one (product C) acting as an estrus synchronizer. The product administered orally at a rate of 40 mg per animal for 18 days. The day following the last distribution of the product, a dose of 1 mg of product A per kg of animal weight was administered sub-cutaneously.

Determination was carried out using standard methods: Plasmatic progesterone; its proportion increases from 1 to 10 ng/ml during the luteal phase and was measured by radio-immunology after plasmatic extraction with ether. Luteinizing hormone or LH; its proportion increases from 5 to 30 ng/ml 6 to 12 hours before ovulation and was measured by radio-immunology directly on the plasma. Estradiol; its proportion increases from 2 to 20 pg/ml during the estral phase. This test procedure is summarized in the following table:

TIME TABLE

| DAYS | OPERATIONS |
|---|---|
| D-13: | blood sample 1 tube 10 ml on heparin: verification of estral cycle |
| D-3: | blood sample 1 tube 10 ml on heparin: progesterone determination |
| D-2: | progesterone determination results; choice of 8 heifers; |
| | PRODUCT C |
| D 0: | sample before treatment; 2 tube on heparin; determination of progesterone and product C; beginning of distribution of product C orally |
| | (after product C) |
| D 1: | sample 2 tubes on heparin; continued distribution of product C |
| D 8: | sample 2 tubes on heparin |
| D15: | sample 2 tubes on heparin |
| D17: | last distribution of product C |
| | PRODUCT A |
| | Injections of product A |
| D18: | −17 H: sample 2 tubes on heparin; determination of estradiol - LH - progesterone |
| D19: | −8 H. −14 H. −20 H: sample 2 tubes on heparin; determination of estradiol - LH - progesterone |
| D20: | −8 H. −14 H. −20 H: sample 2 tubes on heparin; determination of estradiol - LH - progesterone |
| D21: | −8 H. −14 H. −20 H: sample 2 tubes on heaprin; determination of estradiol - LH - progesterone |
| D22: | −8 H. −14 H: sample 2 tubes on heaprin; determination of estradiol - LH - progesterone |

The results represented on the diagram of FIG. 1 indicate that all the heifers came on season in a very short time and the proportion of LH rose extremely quickly. In the same way, biological tests were carried out with the products of the above examples.

Various modifications of the method of the invention may be made without departing from the spirit or scope thereof and it is to be understood that the invention is intended to be limited only as defined in the appended claims.

What we claim is:

1. A method of stimulating ovulation in female warm-blooded breeding animals comprising administering after a progesterone or progestomimetic treatment to female warm-blooded breeding animals in need of ovulation stimulation an ovulation stimulating effective amount of at least one anti-progestomimetic compound of the formula

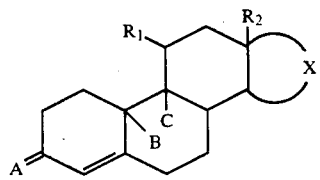

wherein $R_1$ is a hydrocarbon of 1 to 18 carbon atoms optionally interrupted by at least one heteroatom and linked to the steroid nucleus by a carbon atom, $R_2$ is a hydrocarbon of 1 to 8 carbon atoms, X is the remainder of a 5 carbon ring optionally unsaturated and optionally substituted, A is selected from the group consisting of free or ketal protected oxo.

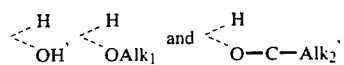

$=NOH$, $=NOAlk_3$ and $=CH_2$, $Alk_1$, $Alk_2$ and $Alk_3$ are individually alkyl of 1 to 8 carbon atoms or aralkyl of 7 to 15 carbon atoms, B and C form a double bond or are —O— and their non-toxic, pharmaceutically acceptable salts with acids and bases.

2. The method of claim 1 wherein $R_1$ is a hydrocarbon of 1 to 18 carbon atoms optionally interrupted by at least one member of the group consisting of nitrogen, sulfur, phosphorus and silicium and optionally substituted with an acyl.

3. The method of claim 1 wherein B and C form a double bond.

4. The method of claim 1 wherein $R_2$ is methyl.

5. The method of claim 1 wherein A is $=O$.

6. The method of claim 1 wherein $R_1$ is substituted aryl or aralkyl.

7. The method of claim 1 wherein $R_1$ is selected from the group consisting of

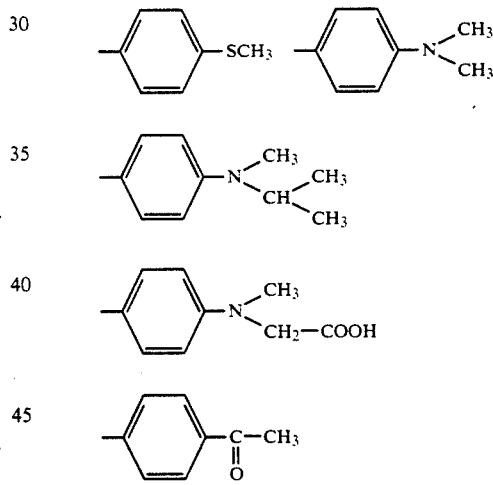

and if appropriate in salified form.

8. The method of claim 1 wherein X is the remainder of

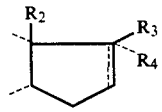

wherein $R_3$ and $R_4$ are individually selected from the group consisting of hydrogen, —OH, $OAlk_4$, —O-$COAlk_5$, alkenyl and alkynyl of 2 to 8 carbon atoms optionally substituted with halogen, —CO—CH$_2$—OH, —CO—CH$_2$—O—CO—Alk$_4$, —CO—COOH-,—CO—COOAlk$_7$, —CHO, —CN and —CO—N-HAlk$_8$, Alk$_4$, Alk$_5$, and Alk$_8$ are alkyl of 1 to 8 carbon atoms or aralkyl of 7 to 15 carbon atoms, Alk$_7$ is alkyl ot 1 to 8 carbon atoms, or $R_3$ is selected from the group consisting of —OH, —OAlk$_4$ and —OCOAlk$_5$ and $R_4$ is —B—O—CO—A'—Z, A' is selected from the group consisting of a bivalent aromatic and optionally unsaturated bivalent aliphatic of 1 to 6 carbon atoms optionally interrupted or terminated with a bivalent aromatic, B is an optionally unsaturated bivalent aliphatic of 1 to 8 carbon atoms, Z is —COOH optionally salified with an alkali metal, alkaline earth metal, —NH$_4$ or an amine or R$_3$ is —CO—A'—Z and R$_4$ is selectef from the group consisting of —C≡C—R$_5$, —CH=CH—R$_5$ and —CH$_2$—CH$_2$—R$_5$, R$_5$ is selected from the group consisting of hydrogen, halogen, trialkylsilyl of 3 to 12 carbon atoms, alkyl to 1 to 6 carbon atoms and phenyl, the latter two being optionally substituted or R$_3$ and R$_4$ together with the carbon atom to which they are attached form a member of the group consisting of

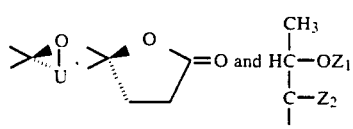

U is —(CH$_2$)$_{n2}$— or —CH=CH—(CH$_2$)$_{n3}$—, n$_2$ is 1, 2, 3 or 4, n$_3$ is 1 or 2, Z$_2$ is alkyl of 1 to 8 carbon atoms and Z$_1$ is selected from the group consisting of hydrogen, alkyl of 1 to 8 carbon atoms and acyl of an organic carboxylic acid of 1 to 8 carbon atoms.

9. The method of claim 1 wherein X is the remainder of

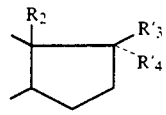

wherein R'$_3$ is selected from the group consisting of —OH and optionally salified —CO—(CH$_2$)$_2$—COOH and R'$_4$ is selected from the group consisting of alkenyl and alkynyl of 2 to 4 carbon atoms, —CH=CH—CH$_2$—O—CO—(CH$_2$)$_2$—COOH and —C≡C—CH$_2$—O—CO—(CH$_2$)$_2$—COOH, both optionally salified.

10. The method of claim 1 wherein the compound is selected from the group consisting of 11β-[4 (dimethylamino)-phenyl]-17α-(1-propynyl)-estra-4,9-dien-17β-ol-3-one and 11β-[4 (dimethylamino)-phenyl]-17α-[(Z)-1-propenyl]-estra-4,9-dien-17β-ol-3-one.

11. The method of claim 1 wherein it is after a progesterone treatment.

12. The method of claim 1 wherein the anti-progestomimetic compound is administered after a treatment with a 17α-allyl-estra-4,9,11-trien-17β-ol-3-one.

13. The method of claim 1 wherein the anti-progestomimetic compound is administered afte an estrus synchronization treatment.

14. The method of claim 1 wherein the breeding animal is a cow.

15. The method of claim 1 wherein the breeding animal is a heifer.

* * * * *